(12) United States Patent
Mijovic et al.

(10) Patent No.: US 10,874,356 B2
(45) Date of Patent: Dec. 29, 2020

(54) WIRELESS EEG HEADPHONES FOR COGNITIVE TRACKING AND NEUROFEEDBACK

(71) Applicant: MBRAINTRAIN LLC BELGRADE, Belgrade (RS)

(72) Inventors: Bogdan Mijovic, Belgrade (RS); Ivan Gligorijevic, Belgrade (RS); Dejan Popovic, Belgrade (RS); Maarten De Vos, Duffel (BE)

(73) Assignee: MBRAINTRAIN LLC BELGRADE, Belgrade (RS)

( * ) Notice: Subject to any disclaimer, the term of this patent is extended or adjusted under 35 U.S.C. 154(b) by 89 days.

(21) Appl. No.: 15/770,148

(22) PCT Filed: Oct. 21, 2016

(86) PCT No.: PCT/RS2016/000011
§ 371 (c)(1),
(2) Date: Apr. 20, 2018

(87) PCT Pub. No.: WO2017/069644
PCT Pub. Date: Apr. 27, 2017

(65) Prior Publication Data
US 2019/0053766 A1 Feb. 21, 2019

(30) Foreign Application Priority Data
Oct. 22, 2015 (RS) .................. P-2015/0679

(51) Int. Cl.
*A61B 5/04* (2006.01)
*A61B 5/00* (2006.01)
(Continued)

(52) U.S. Cl.
CPC .......... *A61B 5/7278* (2013.01); *A61B 5/0006* (2013.01); *A61B 5/02055* (2013.01);
(Continued)

(58) Field of Classification Search
CPC .............. A61B 5/7278; A61B 5/02055; A61B 5/04842; A61B 5/04845; A61B 5/7282;
(Continued)

(56) References Cited

U.S. PATENT DOCUMENTS

2012/0029379 A1* 2/2012 Sivadas ................ A61B 5/0482
600/545
2014/0221866 A1 8/2014 Quy
(Continued)

OTHER PUBLICATIONS

International Search Report received in PCT International Application No. PCT/RS2016/000011, dated May 10, 2017, 5 pages.

*Primary Examiner* — Amanda K Hulbert
*Assistant Examiner* — Natasha Patel
(74) *Attorney, Agent, or Firm* — Rathe Lindenbaum LLP

(57) ABSTRACT

The proposed invention relates to a mobile device and methods for acquisition of biophysiological signals for the purpose of assessing mental states. The said mobile device is embedded into wireless headset that comprises headphones. The mobile device comprises sensors for biophysiological signal acquisition, including, but not limited to, electroencephalographic (EEG) signals, pulse oximetry, heart rate, body temperature and electrodermal activity. Furthermore, the device also measures environmental factors, including, but not limited to, ambient light and sound from the environment. The mobile device administers sound and visual stimuli to the user. The said biophysiological signals, after being processed, are used to assess mental states of the user (emotional states and cognitive processes). Furthermore, the intensity of the said mental states can be maintained at the same level, enhanced or weakened or fully modified using visual or sound stimuli. The device is designed so that it maintains the ergonomics and compactness of the device, so that it can be generally accepted as an everyday consumer device.

29 Claims, 14 Drawing Sheets

(51) Int. Cl.

| | |
|---|---|
| *A61B 5/0478* | (2006.01) |
| *A61B 5/16* | (2006.01) |
| *A61B 5/0205* | (2006.01) |
| *A61B 5/0484* | (2006.01) |
| *H04R 1/10* | (2006.01) |
| *A61B 5/024* | (2006.01) |
| *A61B 5/1455* | (2006.01) |
| *A61B 5/048* | (2006.01) |
| *A61B 5/11* | (2006.01) |

(52) U.S. Cl.
CPC ........ *A61B 5/0478* (2013.01); *A61B 5/04842* (2013.01); *A61B 5/04845* (2013.01); *A61B 5/165* (2013.01); *A61B 5/6815* (2013.01); *A61B 5/7282* (2013.01); *H04R 1/1041* (2013.01); *A61B 5/02438* (2013.01); *A61B 5/048* (2013.01); *A61B 5/0531* (2013.01); *A61B 5/0533* (2013.01); *A61B 5/1112* (2013.01); *A61B 5/14552* (2013.01); *A61B 5/6803* (2013.01); *A61B 2560/0242* (2013.01); *A61B 2560/0247* (2013.01); *A61B 2562/0204* (2013.01); *A61B 2562/0209* (2013.01); *A61B 2562/0219* (2013.01); *A61B 2562/0223* (2013.01)

(58) Field of Classification Search
CPC ..... A61B 5/0006; A61B 5/0478; A61B 5/165; A61B 5/6815; A61B 5/6803; A61B 2560/0242; A61B 5/0533; A61B 5/048; A61B 5/0531; A61B 5/1112; A61B 2560/0247; A61B 2562/0204; A61B 2562/0209; A61B 2562/0219; A61B 2562/0223; A61B 5/02438; A61B 5/14552; H04R 1/1041
See application file for complete search history.

(56) References Cited

U.S. PATENT DOCUMENTS

| | | | |
|---|---|---|---|
| 2014/0257073 A1* | 9/2014 | Machon | A61B 5/6803 600/383 |
| 2015/0282760 A1* | 10/2015 | Badower | A61B 5/6803 600/383 |
| 2015/0297109 A1* | 10/2015 | Garten | A61B 5/0482 600/544 |
| 2018/0228394 A1* | 8/2018 | Tansey | A61B 5/04845 |

\* cited by examiner

FIGURE 3
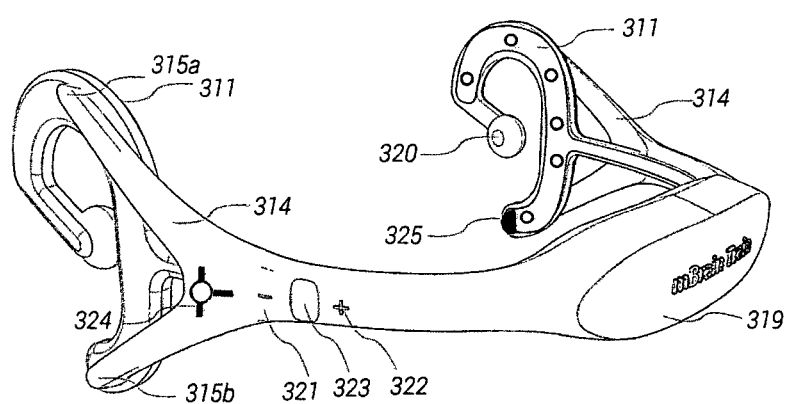
figure 3a
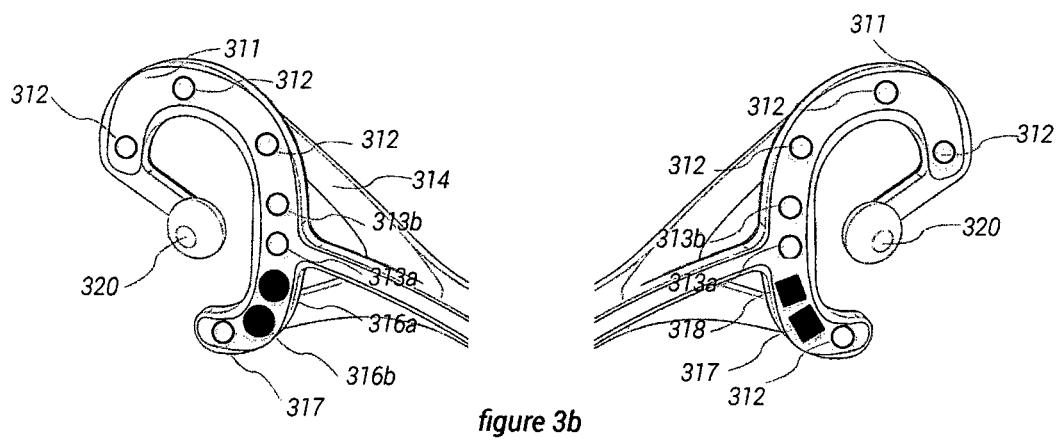
figure 3b

FIGURE 5
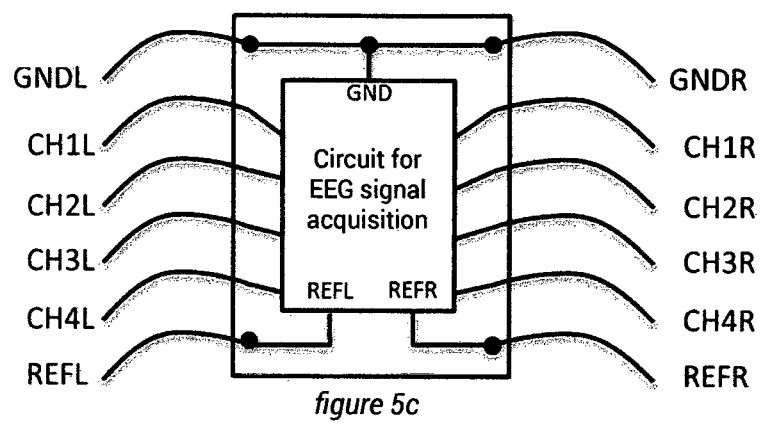
figure 5c
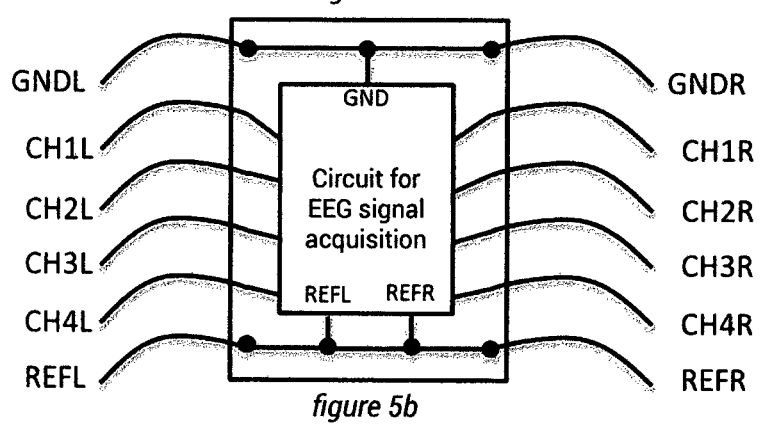
figure 5b
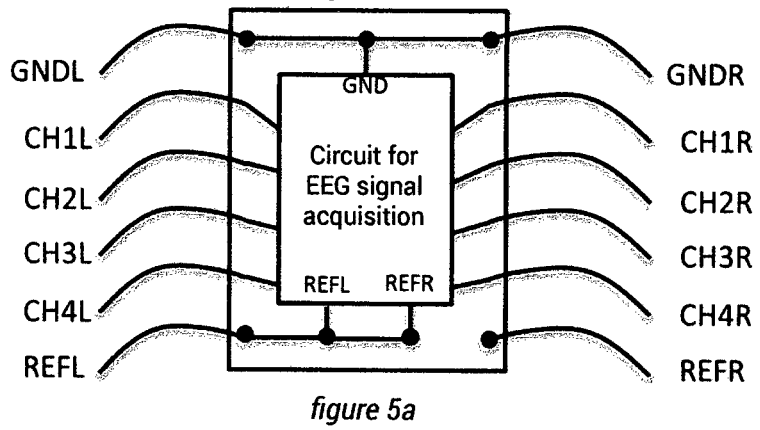
figure 5a

WIRELESS EEG HEADPHONES FOR COGNITIVE TRACKING AND NEUROFEEDBACK

CROSS-REFERENCE TO RELATED APPLICATIONS

This application is a U.S. National Stage entry of PCT Application No. PCT/RS2016/000011 filed Oct. 21, 2016, which claims priority to Serbian Patent Application No. P-2015/0679, filed Oct. 22, 2015, the contents of which are incorporated herein by reference in their entirety.

TECHNICAL FIELD

The proposed invention relates to a system comprising a mobile device that is worn on the head, that enables acquisition of biophysiological signals and wirelessly transmits the acquired signals to the device for processing, display and storage of biophysiological signals in order to determine mental states (cognitive processes and emotional states).

According to the International Patent Classification (IPC) system this patent belongs to: G06Q 50/00 and G06Q 90/00

BRIEF SUMMARY OF THE INVENTION

Biophysiological signals in the proposed invention are in particular electroencephalographic (EEG) signals, the signals for measuring heart rate, blood oxygenation, body temperature, electrodermal response, and methods for processing the biophysiological signal in order to determine the mental states (cognitive processes and emotional states).

The device, in addition, comprises headphones that are used for cognitive stimulation and optionally a microphone and an ambient light sensor to track the influence of the environment to the user. The processed signals are stored in the history on the central server, so that the current mental state can be compared to the previous mental states and thus allowing to monitor user's progress in time.

BACKGROUND ART

The present invention allows acquiring biophysiological signals, in particular electroencephalographic signals, heart rate signals, blood oxygenation, body temperature and electrodermal activity and transmitting the acquired signals wirelessly for recording and processing in order to determine the mental state (cognitive processes and emotional states). The device proposed in this invention is designed as an integrated, ergonomic and compact solution, which has not been reached in previously proposed solutions.

Although the first electroencephalographic (EEG) recording was made in 1924, the EEG systems have not yet been fully utilized for everyday use, unlike other devices for measuring biophysiological signals (e.g. device for measuring heart rate, blood oxygenation, etc.). This is due to negligible use of EEG devices in general, because of their large size and expensive equipment. On the other hand, existing electroencephalographic devices do not meet the requirements of ergonomics, and are not produced as compact, lightweight, integrated solutions, which is required for everyday use.

With the advancement of electronics, EEG devices have become lightweight and compact enough that they can be designed as fully mobile and portable systems. Such devices are e.g. the ones of the company Emotiv (Epoc system), the Smarting system produced by company mBrainTrain, Nautilus system from G-Tec and others. These devices typically contain wireless transmitters and they transmit the acquired signals to other devices, such as personal computers and portables PCs or mobile ("smart") phones, where the further processing is usually performed. These devices, however, are still used mostly for research purposes, since the requirement to be sufficiently ergonomic and compact, so to be used in an everyday life, are still not resolved.

On the other hand, there were numerous portable devices (wearables) for measuring physiological activities, such as wristband Fitbit, Jawbone wristband, as well as iWatch. These devices, more or less successfully, allow users to monitor their physical activity and physical condition. However, a number of devices intended for measuring cognitive processes (stress, productivity, etc.), as well as emotional states have recently appeared. One such device is the wristband Embrace, produced by Empatica company. The issue with this kind of wearables is that they measure mental states indirectly (by measuring various physiological activities such as heart rate and electrodermal activity), not taking into account the direct brain activity measurements. The reason for this is that the existing electroencephalographic (EEG) systems (used for direct measurement of the brain) are not sufficiently ergonomic and compact, which is necessary for their application as an everyday consumer solution.

Several patents include recording of the EEG signals using mobile systems, some of which rely on carriers around the ears, and some are used specifically to determine emotional state.

US 20110004089 A1 proposes a system aimed to record electroencephalographic (EEG) signals in a mobile environment. The system is carried on the earlobe that supports the carrier electrode, RF circuit for transmitting signals and a system for recording EEG signals. Several different embodiments have been suggested. However, the system suggests the deployment of the electrodes all over the user's head, which requires the deployment of pressure at various points on the head, which significantly compromises compactness and ergonomics.

US 005740812 A proposes a system of neural feedback that is built into a headset. The system comprises electrodes in the middle of the head and headphones, so that the user can simultaneously receive a sound recording through headphones and thus to have electrical activity measured. However, the system is linked to the devices for stimulation and recording by a cable which, together with the fact that there are two electrodes that lie close to the centre of the head and that are connected with the scalp through the hair, significantly compromises ergonomics, compactness and quality of the recorded signal.

U.S. Pat. No. 8,781,570 B2 describes another system of NeuroSky Inc. which represents in one of its embodiments EEG headset with built-in sensors. However, this system assumes the acquisition of EEG signals from the earlobe (curve) and the antihelix section and the tragus, that are not suitable for high-quality signal acquisition, as well as from user's forehead, compromising ergonomics and compactness of the device.

There is a number of designed mobile wireless EEG system patents, such as of company Emotiv Inc. US 20070225585 A1, which also compromises the compactness and ergonomics of mobile EEG devices.

None of these solutions has found its widely acceptance in everyday life due to the fact that issues of ergonomics and compactness, which are of crucial importance, are still not resolved.

However, by the development of new technologies, dimensions of EEG devices have decreased, influencing their mobility and many of the above-listed devices (SMARTING, companies mBrainTrain, EPOC, Emotiv Company Inc., the company Mindwave, NeuroSky Inc. and Muse InteraXon Inc. . . . ) have used this fact to successfully spread among the scientific and research community. This influenced the development of methods and algorithms for processing the electrophysiological data recorded in order to assess mental states and emotions.

Numerous inventions in this field can already be found in the scientific literature, but also in the patents of certain individuals and companies. Those are:

US 005601090 A represents a general procedure for assessing the somatic state using neural networks, by the so-called "brute force" method, where simple measurements obtained by Fourier transform of EEG signals from certain measuring points (electrodes) are fed to the input of the neural network. This patent does not provide specific measures of mental states described in the following patents. In addition, this patent represents the measurement from 6 to 15 Hz, which is a mixture of $\alpha$ (8-13 Hz), $\theta$ (4-8 Hz) and $\beta$ (13-32 Hz) ranges.

US 008473044 B2 defines a device and a method for measuring valence, which describes the ratio of powers in $\alpha$ and $\beta$ bands, measured on the left and right side of the head. In short, the power increase in the $\alpha$ band on the left side in respect to the right side of the head and the power increase in the $\theta$ band on the right side in respect to the left side of the head—gives an indication of positive feelings. Respectively, the power decrease in the $\alpha$ band on the right side in respect to the left and the power decrease in the $\theta$ band on the left side in respect to the right, give an indication of negative feelings.

U.S. Pat. No. 8,764,652 B2 unlike the above-mentioned patents, includes measurement of heart rate as an indicator of mental state (besides data obtained from electroencephalographic measurements). This patent introduces the measurement of mental engagement, which is measured indirectly by the increase of heart rate and increase in the $\alpha$ band power of the EEG signals and the decrease in the $\theta$ band power of the EEG signals indicating the increase of mental engagement.

Some of the methods for biophysiological signal processing for the assessment of mental states and the characteristics of the signals that describe mental states can be found in the following scientific literature:

Wilson, G M, Sasse, M A, 2000a. *Do users always know what's good for them? Utilizing physiological responses to assess media quality.* In: The Proceedings of HCI 2000 People and Computers XIV—Usability or Else! (HCI 2000), pp. 327-339 and Ward, Robert D., and Philip H. Marsden. *Physiological responses to different web page designs.* International Journal of Human-Computer Studies 59.1 (2003): 199-212 describes the effect of stress on heart rate and electrodermal response.

Freeman, G. Frederick et al. *Evaluation of an adaptive automation system using three EEG indices with a visual tracking task.* Biological Psychology 50.1 (1999): 61-76 show the influence of $\alpha$ range (8-13 Hz), $\theta$ range (4-8 Hz) and $\beta$ range (13-32 Hz) on the mental states.

R S Lewis, Weekes N Y, Wang T H. *The effect of a naturalistic stressor on frontal EEG asymmetry, stress, and health.* Biological Psychology 2007 July; 75 (3): 239-47, and James A. Coan and John J. B. Allen. *Frontal EEG asymmetry as a moderator and mediator of emotion.* Biological Psychology, 67 (1-2): 7-49, 2004 present the effects of frontal asymmetry of power a range (8-13 Hz) on the left and right side of the head due to changes in mental states.

Other biophysiological signal processing methods for the purpose of preprocessing, or assessing mental states includes the use of a method of independent components, a method of common spatial patterns and the use of artificial neural networks.

The aforementioned findings are a step forward in the field of assessing the mental state of the user and some of the solutions offered are an integral part of the proposed invention. However, the proposed invention focuses primarily on the problem of ergonomics and compactness in order to spread the utilization of EEG as a device for an everyday use. Also, a set of necessary sensors and their positioning, as well as the combination of the measured values from the aforementioned physiological sensors, are crucial in order to enhance the precision of measured mental states.

DISCLOSURE OF THE INVENTION

This invention is a mobile system for measuring biophysiological signals, such as electroencephalography (EEG), heart rate, blood oxygenation, body temperature and electrodermal activity in order to assess mental states (cognitive processes and emotional states), that is embedded into wireless headset comprising headphones.

Sensors that collect biophysiological signals are placed on the arc carrier behind one or both ears, so they do not burden other parts of head and are not visible on other parts of the head or body. EEG signals are collected using an unspecified number of electrodes that adhere to the scalp behind the ear of a user. The electrodes are such that adhere to the scalp of the patient and do not create uncomfortable pressure. Signals from the electrodes are led by a conductive layer to electrical input circuits for the acquisition of electroencephalographic signals.

Electrodermal activity is also measured with electrodes that are placed on the arc carrier behind the ear, which may essentially be the same electrodes that measure the EEG signals, or they may be specific ones. The measured signal is also fed by the conductive layer into the circuit to measure the electrodermal activity.

Heart rate is measured by processing signals from light sensors, that measure the change in intensity of the light released from the light-emitting diodes (for example, infrared, red and green electrodes) and the light measured on the measuring diode. The measuring diode can measure either the light that passes through the body part that contains blood vessels (such as an earlobe), or the light that is reflected from the body part that contains blood vessels (for example, part of the head behind the ear).

Body temperature is measured by temperature sensors which are miniature infrared cameras and by the amount of radiated infra-red light they determine the exact temperature of the body.

These signals are further led to electrical circuits for further processing and then the processed values are led to the integrated module for wireless transmission of digital signals (e.g. Bluetooth). Such signals are then transmitted wirelessly to devices for receiving and visualization, which are essentially mobile phones or computers.

Also, acquired and processed signals could be transmitted via direct internet connection, for example using a GPRS module, from the device to a central server for processing and storage in the central database, as described in the patent number P-2014-0628 submitted to the Serbian Intellectual Property Office.

This invention proposes a portable device for measuring biophysiological signals, primarily EEG signal (which is a direct measure of electrical activity of the brain), heart rate (which is one of the main indicators of stress), electrodermal activity (which is the fastest physiological response to changes in mental status), and body temperature to assess the mental state of the user. The device has an embedded wireless headset comprising headphones. The device, compared to previous findings, significantly improves the compactness and ergonomics. On the other hand, the position of sensors and a complete set of necessary sensors allow precise assessment of mental states unlike the previous solutions.

Acquired signals may be entirely processed on the recording device, or may be transmitted by a short distance digital data transmission network (such as a Bluetooth network) to a device for processing, display and storage of biophysiological signals which is essentially a mobile phone or personal computer, or may be directly transmitted to a central server for further processing by long distance digital data transmission network (such as the Internet), e.g. by using the GPRS module or Wi-Fi module. The signals could also be partially processed on the device for the acquisition of biophysiological signals on the central server and on the device for processing, display and storage of biophysiological signals.

EEG signal features that are used to measure mental states are the frequency bands: ($\alpha$: 8-13 Hz), ($\beta$: 13-32 Hz), $\gamma$: 32-60 Hz, $\delta$: 1-4 Hz, $\Theta$: 4-8 Hz) and ratios between the frequency bands measured from different measurement points (electrodes) as well as the amplitudes and latencies of certain waves contained in evoked potentials recorded using EEG sensors (such as the P100, N200, P300, N400, or others) that occur as a result of stimuli (visual or auditory), which could be presented to the subject through the headphones embedded in the wireless head set, or using the screen of a mobile phone that the device has established a wireless connection with (e.g. Bluetooth connection) or through a third party device or from the environment. The biophysiological signal acquisition device may comprise sensors for acquiring stimuli from the environment. The sensors for acquiring the stimuli from the environment could be a microphone for sound stimuli acquisition, or an ambient light sensor for acquiring the light stimuli.

Examples of EEG signal processing to assess mental states are numerous and may be found in scientific papers and some of the mentioned patents—in the fore presented BACKGROUND OF THE INVENTION section. For example, good feelings could be measured by differentiation of power (or power ratios) contained in $\Theta$ and $\alpha$ of EEG frequency bands on the right and left side of the head. Excitement can be determined based on the balance of power from $\beta$, $\Theta$ and $\alpha$ range. However, for precise assessment of mental states, it is necessary to use other physiological signals, such as electrodermal activity and heart rate. For example, excitement leads to an increase of the heartbeat. The increase in excitement further leads to an increase in electrodermal conductance, whereas on the other hand idleness leads to the reduction of electrodermal activity. This component is called the tonic component of electrodermal activity. Electrodermal activity contains phasic component, which quickly responds to abrupt external stimuli.

Algorithms for determining mental states generally use only one modality for assessment (such as electroencephalography, or the heart rate, or electrodermal activity). This invention proposes a device that combines different modalities for the assessment of mental states.

After processing and the assessment of mental states, or current mental states as a result to a certain stimulus, the mental states are stored in a database which could be on a mobile phone or a PC, or in a remote central database. In case of using a central database, it is necessary to take into account the privacy of the stored biophysiological data.

Although the system could be used for neuromarketing, assistive personalized learning, therapeutic, as well as medical and other diagnostic purposes, the primary use of this invention is the quantification and monitoring of mental states of a user in order to maintain mental health, increase productivity and reduce stress levels. The system could be monitored by applicative software or a platform that makes certain recommendations in order to improve mental functioning and increase focus and operating efficiency and a better use of time. Also, application software, or platform, could provide a variety of other recommendations (such as automatically recommending the user to play music through wireless headphones) estimated on the basis of the mental state of the user, and taking into account the preferences of the user based on the measured mental states in the past.

Therefore, in the main aspect of this invention, a mobile device and the method for acquisition of biophysiological signals from FIG. 1 are provided for the purpose of assessing mental states of the user, that is embedded in the wireless headset comprising headphones, while maintaining the ergonomics and compactness of the device.

In another aspect of the invention, a mobile system for the acquisition of biophysiological signals is provided in order to assess mental states comprising: a mobile device for the acquisition of biophysiological signals, a central server, a central database and a device for processing, display and storage of biophysiological signals, as well as a method of connecting a mobile device for the acquisition of biophysiological signals with the central server and the central database and with the devices for processing, display and storage of biophysiological signals.

In the third aspect of the present invention, a mobile system and a method for assessing the mental states as a result of external sound stimuli is provided.

In the fourth aspect of the present invention, a mobile system and a method for assessing the mental states as a result of external visual stimuli is provided.

In the fifth aspect of the present invention, a mobile system and a method for assessing the mental states as a result of influence from the environment is provided.

In the sixth aspect of the invention, a mobile system and a method for modifying the sound stimuli presented to the user is provided in order to maintain or change a mental status (for example, the purpose of music therapy or music recommendation system).

In the seventh aspect of the present invention, a mobile system and a method for modifying the visual stimuli presented to the user is provided in order to maintain or change a mental state (e.g. for the purpose of visual therapy).

In an alternative embodiment, the axle that is located around the user's ear in the mobile device for acquisition of biophysiological signals as in FIG. 1, are running above the user's head.

In yet another alternative embodiment, a mobile system for the acquisition of biophysiological signals in order to assess the mental states does not contain a central server and a central database, but only a biophysiological signal acquisition device and a device for processing, display and storage of biophysiological signals.

In another alternative embodiment, the mobile system for acquisition of biophysiological signals in order to assess the mental states does not contain a device for processing, display and storage of biophysiological signals, but only a mobile device for the acquisition of biophysiological signals, the central server and a central database.

In another alternative embodiment, the mobile system for the acquisition of biophysiological signals in order to assess mental states does not contain a device for processing, display and storage of biophysiological signals nor a central server nor a central database, but only a device for the acquisition of biophysiological signals and the procedure for processing biophysiological signals in order of determination of mental states.

In yet another alternative embodiment, the headset comprising the mobile device for the acquisition of the biophysiological signals does not contain headphones and is intended to be used for medical diagnostic purposes, such as, for example, monitoring of patients who are being diagnosed for epilepsy, or monitoring of patients diagnosed with epilepsy.

The need for the proposed system of the present invention arises primarily from the fact that the current systems for collecting biophysiological signals (primarily electroencephalographic signals) do not meet the requirements of ergonomics and compactness, which are necessary in order to be used in everyday life, and, therefore, today's users do not have possibility of daily monitoring their mental state. If such a system should be found in a daily use in the long run it could become a useful tool for personal health care, diagnosis and prevention of the user. Also, such a system would allow auditory or visual therapy as a maintenance of the same mental state or a change in mental state. Further, such a device, taking into account that it is embedded in a wireless headset containing headphones, would allow the construction of a system for recommending music that the user would like to listen to at a given time, based on the current mental state compared to previous mental states and preferences of users according to a specific musical genre.

Other and further features, advantages and benefits of the invention will become apparent in the following description taken in conjunction with the following drawings. It is to be understood that the foregoing general description and following detailed description are exemplary and explanatory but are not to be restrictive of the invention. The accompanying drawings are incorporated in and constitute a part of this application and, together with the description, serve to explain the principles of the invention in general terms. Like numerals refer to like parts throughout the disclosure.

BRIEF DESCRIPTION OF DRAWINGS

FIGS. 3a and 3b are schematic representation showing the biophysiological signal acquisition device embedded in a wireless headset containing headphones.

FIGS. 5a, 5b and 5c are examples of the preferred embodiment of the set and the ordering of biophysiological sensors placed against the scalp behind the user's ear.

BEST MODE FOR CARRYING OUT OF THE INVENTION

Figure 1:
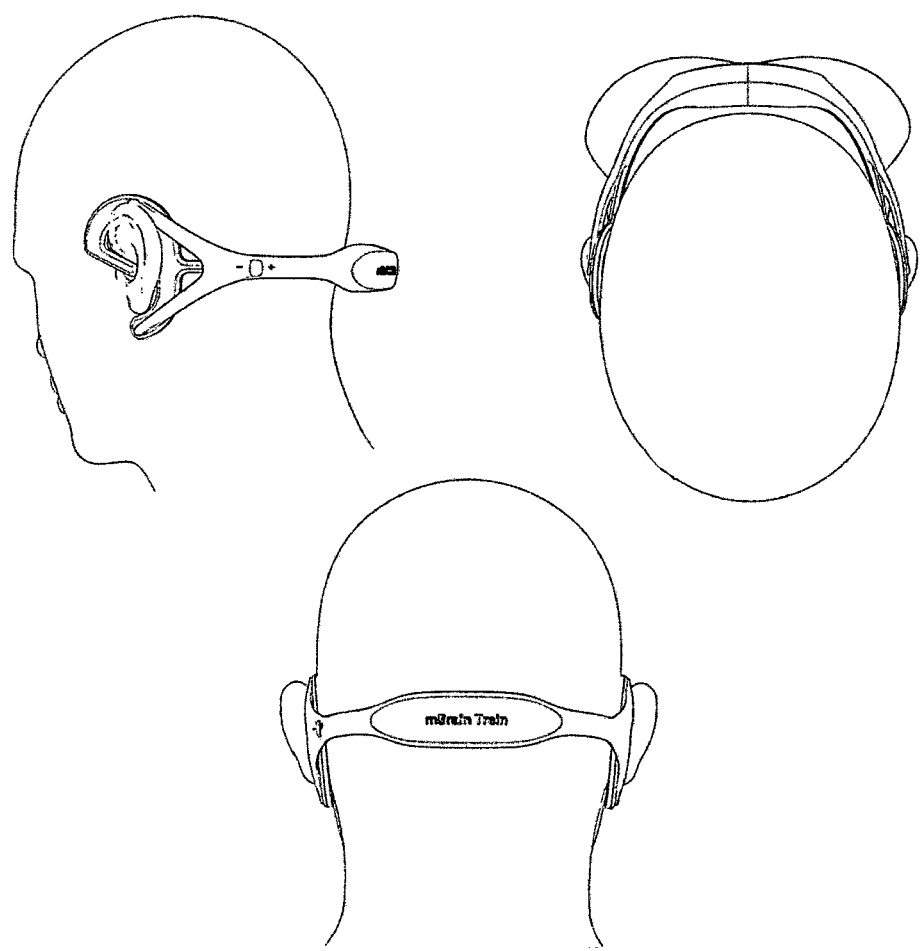
FIG. 1 is a schematic representation showing the biophysiological signal acquisition device embedded in a wireless headset comprising headphones mounted on the head of the user from multiple angles.
Figure 2:
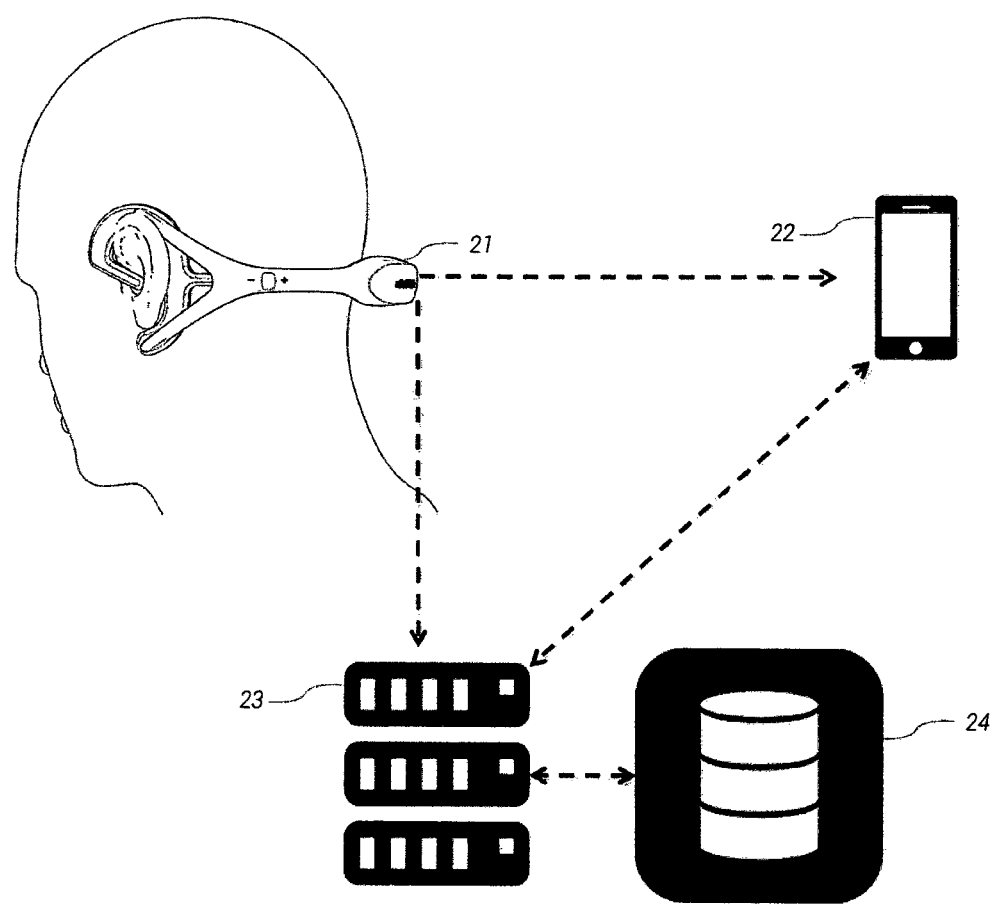
FIG. 2 is a schematic representation showing the mobile system for acquisition of biophysiological signals in order to assess mental states.

FIG. 2 represents a schematic illustration showing a mobile system for biophysiological signals acquisition in order to assess the mental states. The mobile system for biophysiological signals acquisition in order to assess mental states, comprises a biophysiological signal acquisition device 21, a device for processing, display and storage of biophysiological signal 22, the central server 23 and the central database 24.

The biophysiological signal acquisition device 21 is further connected using Bluetooth module for wireless communication, to the device for processing, display and storage of biophysiological signals 22 that can transmit the acquired biophysiological signals in digital format to the devices for processing, display and storage of biophysiological signals 22.

The biophysiological signal acquisition device 21 is further connected by means of the modules for a long distance wireless communication (such as Wi-Fi module or GPRS modules), to the central server 23 that transmits the acquired biophysiological signals together with the metadata in the digital format to the central server 23 via the Internet.

The central server 23 receives the data stored on the biophysiological signal acquisition device 21, to perform further signal processing. The central server 23 is further connected to the central database 24. The central server 23 can store the biophysiological signals in the central database 24. The central server 23 is further able to read data stored in the central database data 24. The central server 23 is connected by means of the module for a long distance wireless communication (such as Wi-Fi module or GPRS modules) to the device for processing, display and storage of the biophysiological signals 22. The central server 23 can transmit the data read from the central database 24 to the device for processing, display and storage of biophysiological signals 22.

The device for processing, display and storage of biophysiological signal 22 is connected to the biophysiological signal acquisition device 21, by the means of modules for of short distance wireless communication, such as Bluetooth.

The device for processing, display and storage of biophysiological signal 22 can receive the biophysiological signals from the biophysiological signal acquisition device 21 and store them in the internal memory, or display them on the screen for displaying, after being optionally previously processed by a signal processing application. Devices for processing, display and storage of biophysiological signal 22 may have a screen for displaying and a memory storage. Devices for processing, display and storage of biophysiological signals 22 further comprises the possibility of short-distance wireless connections (such as, but not limited to, Bluetooth). The device for processing, display and storage of biophysiological signal 22 receives the signals transmitted from the central server 24 by using long-distance wireless communication module (e.g. GPRS or Wi-Fi) and store the recorded signals in the internal memory, or display them on the screen, after they have previously been optionally processed by a signal processing software application.

FIGS. 3a and 3b represent a schematic illustration that show the biophysiological signal acquisition device embedded in the wireless headset comprising headphones, biophysiological signal acquisition device 21 comprises two arc carriers 311, containing at least one measuring electrode adhesive to the skin of the patient or subject for measuring electroencephalographic activity 312, a reference electrode for measuring electroencephalographic activity that adheres to the skin of the patient or subject 313a, and a ground electrode for measuring electroencephalographic activity that adheres to the skin of the patient or subject 313b.

The electrodes are, in particular, designed as not to endanger the compactness and ergonomics of the device. An axle 314 rests on the carriers in at least two different anchor points 315a and 315b and thus applies pressure on the carriers, so that the electrodes 312, 313a, 313b have a better adhesion with the skin of the user's head. The arc carriers are, therefore, designed to apply a small force on the electrodes so that the electrodes remain in contact with the head of the user, but they still continue to satisfy the ergonomics requirements. The biophysiological signal acquisition device further comprises one or more electrical circuits for the acquisition of biophysiological signals, which is an input system for signal acquisition from the biophysiological sensors. The said electrical circuits for recording and processing of biophysiological signals are placed in the body of the mobile device for the acquisition of biophysical signals 319. Biophysiological sensors in particular electrodes for EEG acquisition activity 312, 313a, 313b, electrodes for acquisition of electrodermal activity 316a, 316b, transmissive or reflective light sensors for the acquisition of pulse oximetry 317, sensors for measuring body temperature and other biophysical sensors 318. Biophysiological sensors are in particular designed as not to disturb the compactness and ergonomics of the device. Biophysiological sensors are such that all of the biophysiological sensors are located on the head behind the user's ear.

The biophysiological signal acquisition device comprises movement tracking sensors to track movements of a user of the biophysiological signal acquisition device. Sensors to record the movement of the user using the biophysiological signal acquisition device are, in particular, accelerometers and gyroscopes.

The biophysiological signal acquisition device comprises headphones for auditory stimulation 320. The headphones can be used for the short sound stimulation (in the form of discrete audio signals) and for continuous sound stimulation (such as music).

The biophysiological signal acquisition device further comprises the buttons to turn the headphones volume down 321 or up 322. The buttons to turn the headphones volume down 321 or up 322 are, in particular, implemented using touch-sensitive sensors.

The biophysiological signal acquisition device, in particular, comprises the sensors for acquiring environmental influence. The sensors for acquiring environmental influence are, in particular, sensors to record ambient light 323 (such as ultraviolet light) and sensors for sound recording 324 (microphone). The said signals from the sensors for acquiring environmental influence are synchronized and transmitted together with the acquired biophysiological signals to the device for processing, display and storage of biophysiological signals.

Figure 4:
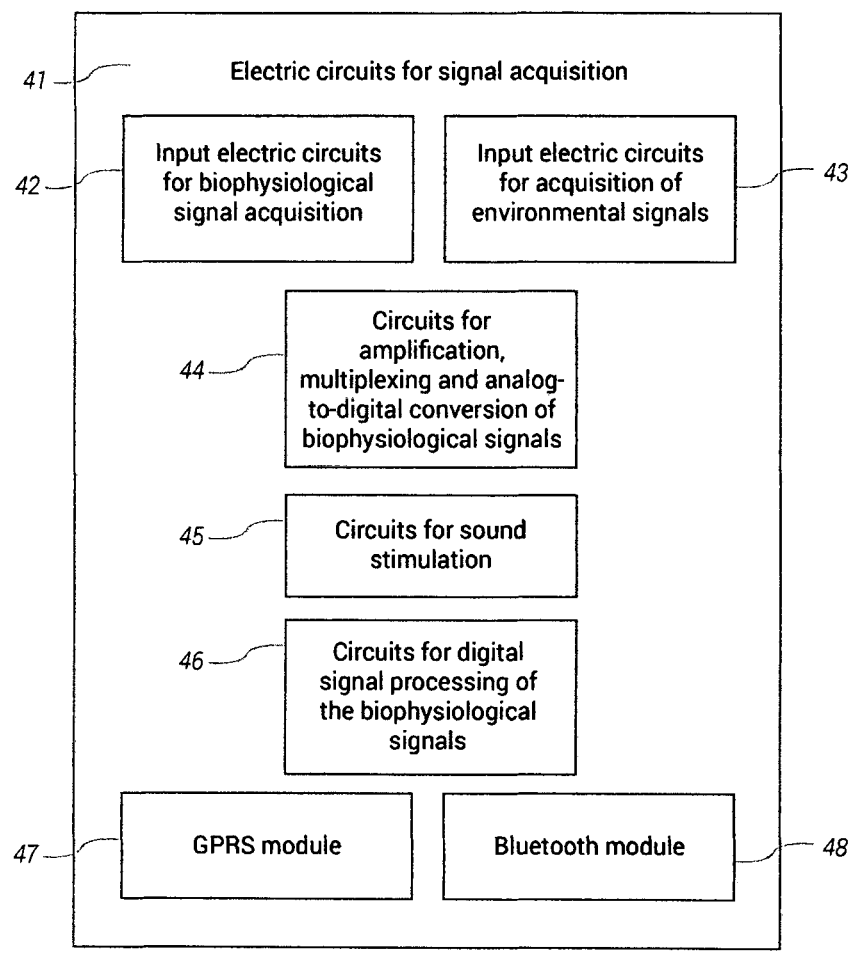
FIG. 4 is a schematic representation showing the electrical composition of the biophysiological signal acquisition device.

FIG. 4 is a schematic representation that shows electrical composition 41 of the biophysiological signal acquisition device 21. The electrical composition 41 of the biophysiological signal acquisition device 21 comprises input electric circuits for biophysiological signal acquisition 42, which is an input system for receiving signals from the electrodes. The input electric circuits for biophysiological signal acquisition 42 comprise various circuits for receiving signals from different biophysiological sensors.

Biophysiological sensors are, in particular, sensors for acquiring electroencephalographic (EEG) signals 32, 33a and 33b, sensors for measuring electrodermal activity 36a and 36b, sensors for measuring pulse oximetry 37, sensors for measuring body temperature 38 and other biophysiological sensors. The electrical composition 41 of biophysiological signal acquisition device 21 further comprises an input electric circuits for acquisition of environmental signals 43. The input electric circuits for acquisition of environmental signals 43 comprise circuits for acquiring signals from ambient light sensor 323 as well as sensors for recording sound (microphones) 324. The electrical composition 41 of the biophysiological signal acquisition device 21 comprises a circuit with amplifier, multiplexer and analogue-to-digital (A/D) converter 44, circuit for sound stimulation 45, circuit for signal processing 46, short-distance wireless communication module as Bluetooth 47, long-distance wireless communication module, such as GPRS module 48. The electrical composition 41 of the biophysiological signal acquisition device 21 can transmit the digitalized acquired electrophysiological signals short-distance to the devices for processing, display and storage of biophysiological signals 22 using short-distance wireless communication modules 47, or to receive information (such as sound recordings) wirelessly from external devices. The electrical composition 41 of the biophysiological signal acquisition device 21 can further transmit the recorded electrophysiological signals, together with the metadata in digital form to a central server 23 via the Internet using the long-distance wireless communication module 48.

The electrical composition 41 of the biophysiological signal acquisition device 21, in particular, receives the sound from external devices, and passes it to a circuit for sound stimulation 45, which then plays the recorded sound to the user through headphones 320.

FIGS. 5a, 5b and 5c are examples of the preferred embodiment depicting collection and arrangement of biophysiological sensors placed against the scalp behind one or, respectively another ear of the user. The set of sensors behind the two ears is not necessarily identical. In the preferred embodiment of this invention 4 electrodes for measuring electroencephalographic activity, 1 reference electrode and one ground electrode are placed on the scalp behind each ear. The reference electrodes can be independent behind both ears, they may be short-circuited, or they may exist only one reference electrode behind one ear.

According to the preferred embodiment, a set of electrodes behind one ear in addition to the electrodes for measuring EEG activity may contain sensors that measure body temperature, as well. A set of electrodes behind one ear in addition to the electrodes for measuring electroencephalographic activity may contain sensors that measure pulse oximetry, heart rate and blood oxygen saturation.

According to the desired embodiment a set of electrodes behind the other ear in addition to the electrodes for measuring electroencephalographic activity may contain a sensor for measuring the electrodermal activity, which must have at least one measuring and one reference electrode.

A set of sensors continuously measure biophysiological activities, but also under certain sound stimuli coming through the headphones. The headphones, in particular, can administer the stimuli continuously (in the form of music, speech, etc.), or in the form of short discrete sounds.

Figure 6:
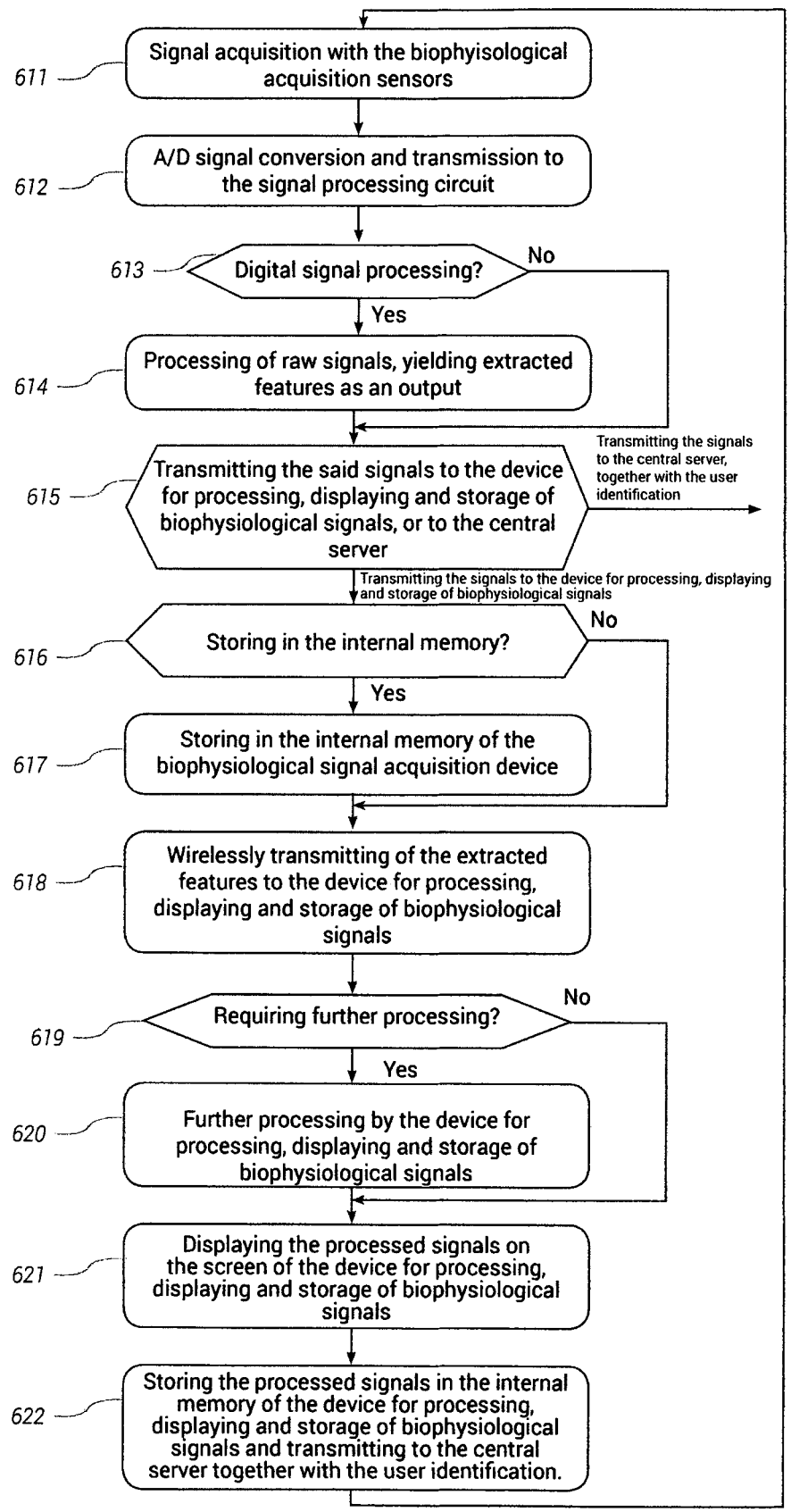
FIG. 6 is a flowchart of the method that processes and transmits the signals obtained from the biophysiological signal acquisition device to the device for processing, display and storage of biophysiological signals where they are further processed, displayed on the screen, stored in memory and transmitted to a central server for further processing and storage in the central database.

FIG. 6 is a complete operation diagram of the method that processes and transmits the signals obtained from the biophysiological signal acquisition device to the device for processing, display and storage of biophysiological signals, where they may be further processed, displayed on the screen, stored in memory in the form of mental states or processed biophysiological signals, and then transmitted to the central server for further processing and storage in a central database in the form of mental states or processed biophysiological signals.

Step 611: The sensors perform the acquisition of biophysiological signals, whereby biophysiological signals can be electroencephalographic signals or light signals, to measure pulse oximetry, or electrodermal activity signals or signals for measuring body temperature. Biophysiological signals may be one or all of, or a combination of these signals.

Step 612: A/D conversion is performed for the signals that are by definition analogue (such as electroencephalographic signals and signals conducting measuring of electrodermal activity and signals for measuring temperature).

Step 613: Choosing whether digital biophysiological signal processing is being performed.

Step 614: Processing of the collected digital signals is performed, in the case that option is chosen in step 613. The processing of the collected digital signals may be, in particular, the signal filtering with high or low pass filters, or a combination of these filters. Digital signal processing may further be, in particular, statistical signal processing (for example, using methods such as independent component analysis or a common spatial patterns or other). Signal processing may, as an output, provide either temporal processed signals, or only the characteristics of the processed signals, such as the power of a certain frequency band, or it may be a specific mental states.

Step 615: Choosing whether the collected and processed data is transmitted to the device for processing, display and storage of biophysiological signals or stored in the internal memory of the mobile device for the acquisition of biophysiological signals, in order to be transmitted to the central server, later.

Step 616: Choosing whether the digital data are stored in the internal memory of the mobile device for the acquisition of biophysiological signals.

Step 617: The recorded and processed biophysiological signals are stored in the internal memory of the mobile device for the acquisition of biophysiological signals in the case that this option was selected at the step 616.

Step 618: The processed signals are transmitted to the device for processing, display and storage of biophysiological signals. The processed signals are, in particular, temporal signals or signal characteristics, such as the power of a certain frequency band or calculated mental states.

Step 619: Choosing whether the device for processing, display and storage of biophysiological signals performs further signal processing.

Step 620: The further digital signal processing is performed in the device for processing, display and storage of biophysiological signals in case this option was selected in step 619. Processing of digital signals on the device for processing and storage of biophysiological signals may be signal filtering with certain high or low pass filters or a combination of these filters. Signal processing may be, in particular, statistical signal processing (for example, using methods such as independent component analysis and common spatial patterns or other). Signal processing may, in particular, have an output which could provide either temporal processed signals, or only the characteristics of the processed signal, such is the power of a certain frequency band, or mental states. The aforementioned signal processing in no way excludes the possibility of implementation of additional digital signal processing algorithms.

Step 621: The processed signal is displayed on the display of the device for processing, display and storage of biophysiological signals.

Step 622: The processed signal is stored in the memory of the device for processing, display and storage of biophysiological signals and transmitted to the central server, along with the identification of the user, for further processing and storage in the central database.

Figure 7:
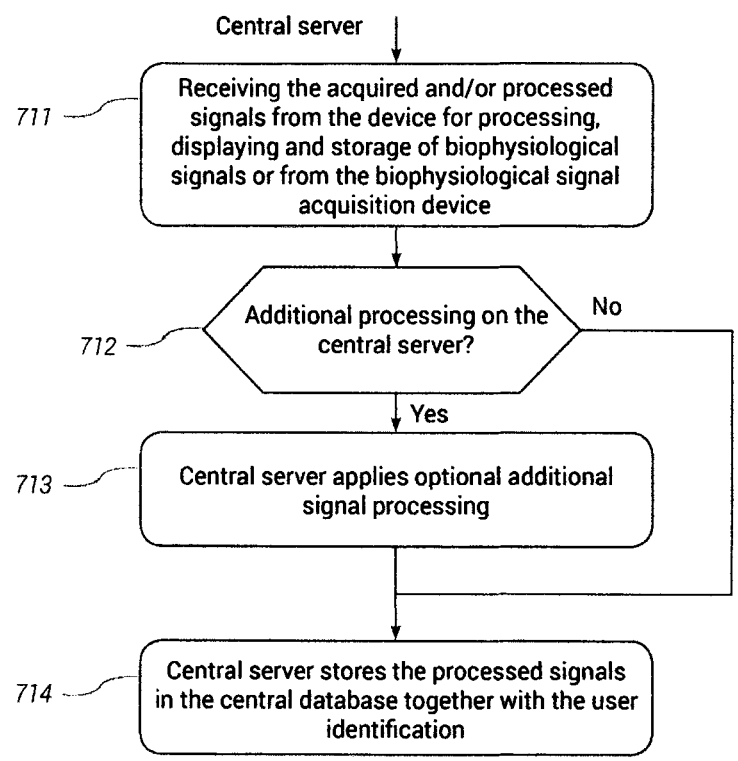
FIG. 7 is a flowchart of the storing the recorded data into a central database by a central server.

FIG. 7 is a complete operation diagram of the recorded data storage process in a central database.

Step 711: the central server receives the data transmitted by the biophysiological signal acquisition device, or by the device for processing, display and storage of biophysiological signals. The data are, in particular, the signals that may be unprocessed signals, processed signals or isolated signal characteristics obtained by processing of biophysiological signals, or calculated mental states. The data in particular comprise the identification of the user.

Step 712: Choosing whether the central server is required to perform additional digital signal processing.

Step 713: The central server performs further processing of the collected biophysiological signals in case that this option is selected in step 712. Further processing on the central server may be performed only on a set of data that is received during the current data transfer, or it can be combined with previously collected data, for example using algorithms for machine learning. Previously collected data, in particular, belongs to the same user as the current data, or they belong to a group of users, or they belong to all users. User's data in the database is determined on the basis of user identification.

Step 714: The central server stores the processed and/or unprocessed data to the central database together with the identification of the user.

Figure 8:
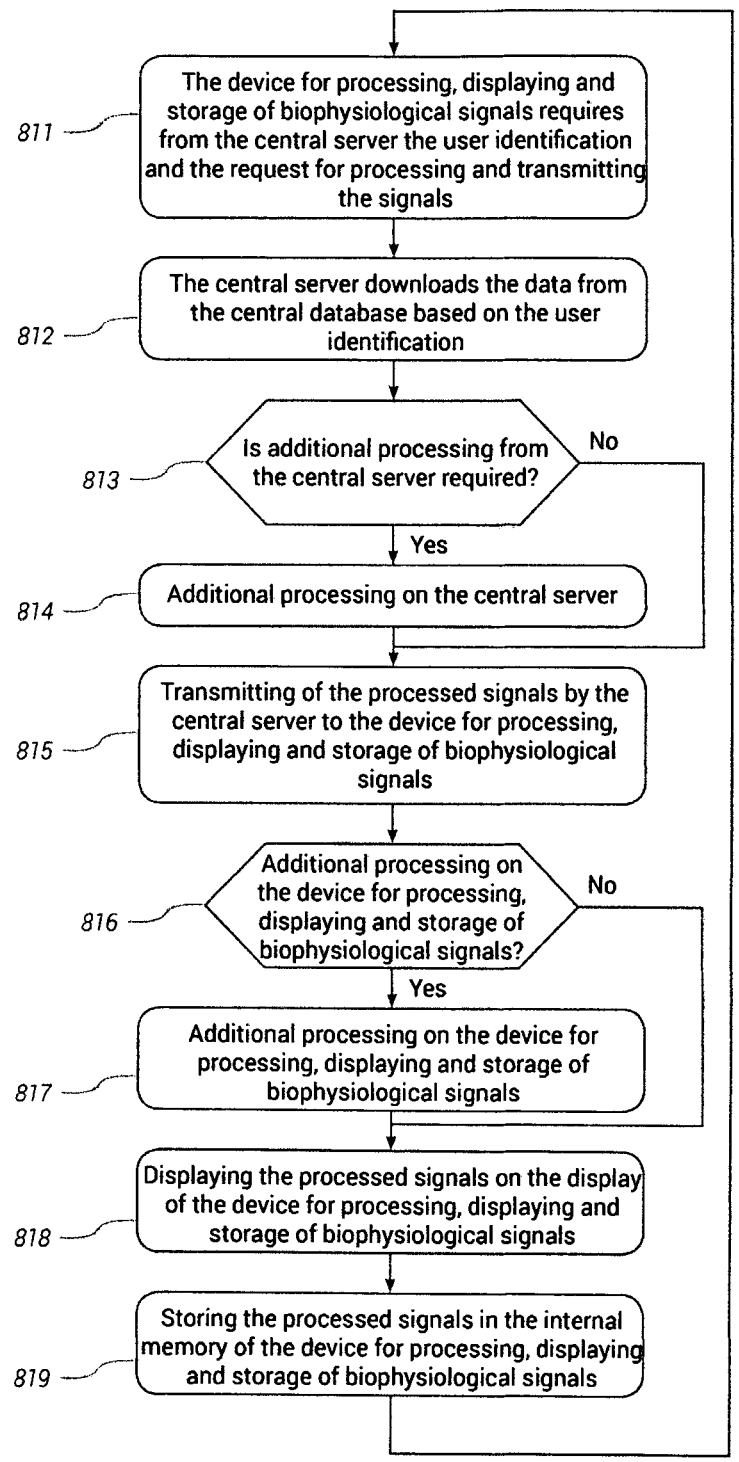
FIG. 8 is a flowchart of the transmitting the processed data by the central server to the device for processing, display and storage of biophysiological signals.

FIG. 8 is a complete operation diagram of transmitting the processed data from the central server to the device for processing, display and storage of biophysiological signals.

Step 811: the device for processing, display and storage of biophysiological signals transmits to the central server user's identification and requirements for optional processing and obtaining data from the central database.

Step 812: The central server, based on the user identification accepts data from the central database for processing and their transmission to the device for processing, display and storage of biophysiological signals.

Step 813: The selection is made whether to require additional processing at the central server.

Step 814: If additional data processing was required by the central server in step 813, the central server performs additional processing of the said data from the central database and prepares them for transmitting to the device for processing, display and storage of biophysiological signals. The processing on the central server, in particular, can be done only on a set of data that has been received during the current data transfer, or it can be combined with previously collected data, for example using algorithms for machine learning. Previously collected data are characterized as belonging to the same user, or belonging to a group of users, or belonging to all users. Belonging of the data in the database is determined on the basis of user identification.

Step 815: The central server transmits the processed data to the device for processing, display and storage of biophysiological signals.

Step 816: The selection is made whether to request further processing on the device for processing, display and storage of biophysical signals.

Step 817: The device for processing, display and storage of biophysiological signals performs additional signal processing of the biophysiological signals in case it was required by the user.

Step 818: The device for processing, display and storage of biophysiological signals displays processed biophysiological signals on the display of the device for processing, display and storage of biophysiological signals.

Step 819: The device for processing, display and storage of biophysiological signals stores processed biophysiological signals in the memory of the device for processing, display and storage of biophysiological signals.

Steps 811 to 819 could be repeated for an indefinite number of times. Processing the biophysiological signals is, in particular, the calculation of the mental states.

Figures 9, 9A, 9B:
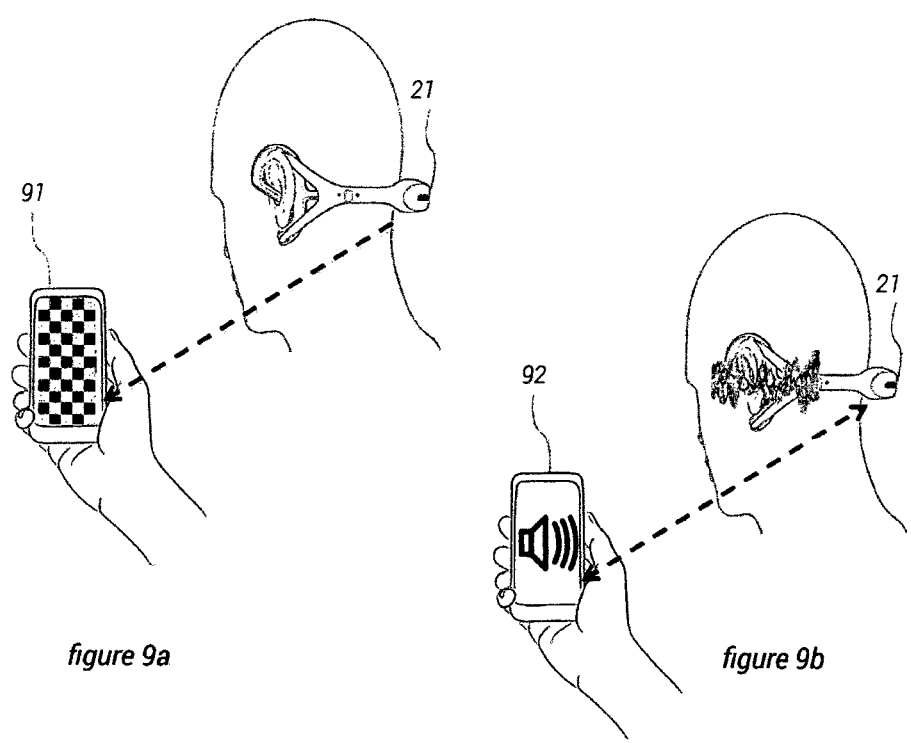
FIGS. 9a, 9b are flowcharts of biophysiological signal acquisition as a result of biofeedback to external (visual or auditory) stimuli.

FIGS. 9a, 9b are schematic representations of acquiring biophysiological signals as a result of biological feedback to external stimuli. In one embodiment, the external stimuli are in particular visual stimuli (FIG. 9a) displayed on the display of the device for visual stimulation. In another embodiment, the external stimuli are, in particular, the sound stimuli that can be released through the headphones that are comprised in a wireless head set with embedded mobile device for measuring biophysiological signals in order to assess mental states.

Figure 10:
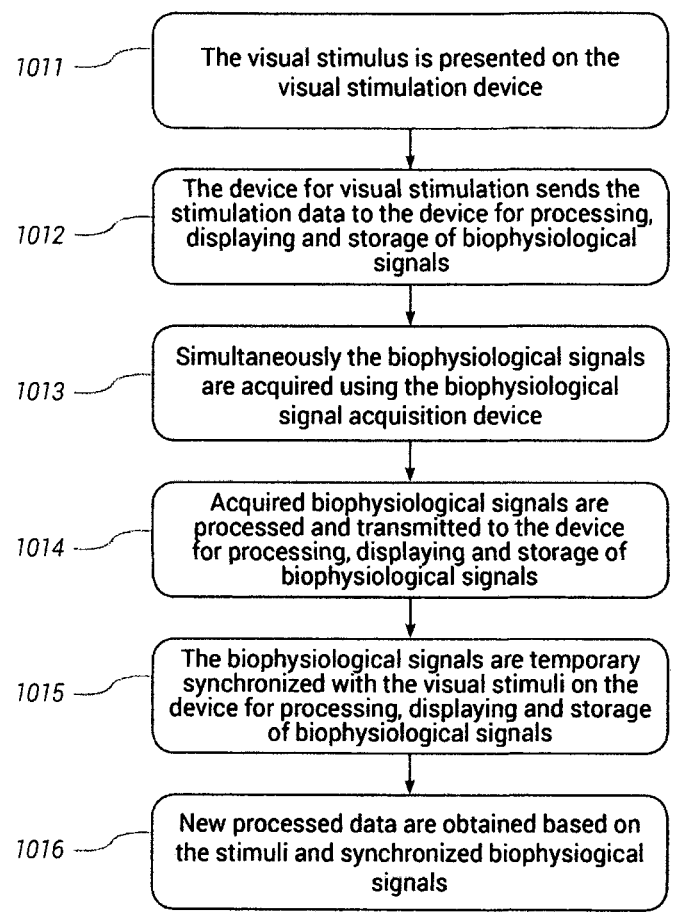
FIG. 10 is a flowchart of biophysiological signals acquisition as a result of biofeedback controlled with visual stimuli.

FIG. 10 is a complete operational diagram of collecting biophysiological signals as a result of biological feedback induced by a visual stimuli.

Step 1011, the visual stimulus is displayed on the display of the device for visual stimulation. The device for visual stimulation is essentially a smartphone. The device for visual stimulation is essentially the same device as the device for processing, display and storage of biophysiological signals. The visual stimulation can be, in particular, administered for the purpose of biological feedback via software applications for biological feedback. Visual stimulation can be, in particular, a simple view on the screen of the device for visual stimulation. For example, if the device for visual stimulation is a smart phone, the visual stimulus could be previewed as any content from various mobile applications or web content, such as news or video content or any other content that could be displayed on a mobile phone screen. Visual stimulation, therefore, may also be cognitive, not only purely visual stimulation.

Step 1012: The data describing the visual stimulation are transmitted from the device for visual stimulation device to the device for processing, display and storage of biophysiological signals.

Step 1013: the biophysiological signal acquisition device 21, acquires biophysiological signals simultaneously with the step 1012.

Step 1014: the biophysiological signal acquisition device 21 transmits acquired biophysiological signals to the device for processing, display and storage of biophysiological signals, as shown in FIG. 2.

Step 1015: The device for processing, display and storage of biophysiological signal processes the signals in a manner to be time-synchronized with the data for visual stimulation and optionally perform additional signal processing.

Step 1016: Based on the processing performed in the step 1015, the new, processed biophysiological signals are obtained that could be displayed on the screen of the device for processing, display and storage of biophysiological signals, or they could be stored in the internal memory of the device for processing, display and storage of biophysiological signals or may be transmitted to the central server.

The processed physiological signals are, in particular, mental states.

Figure 11:
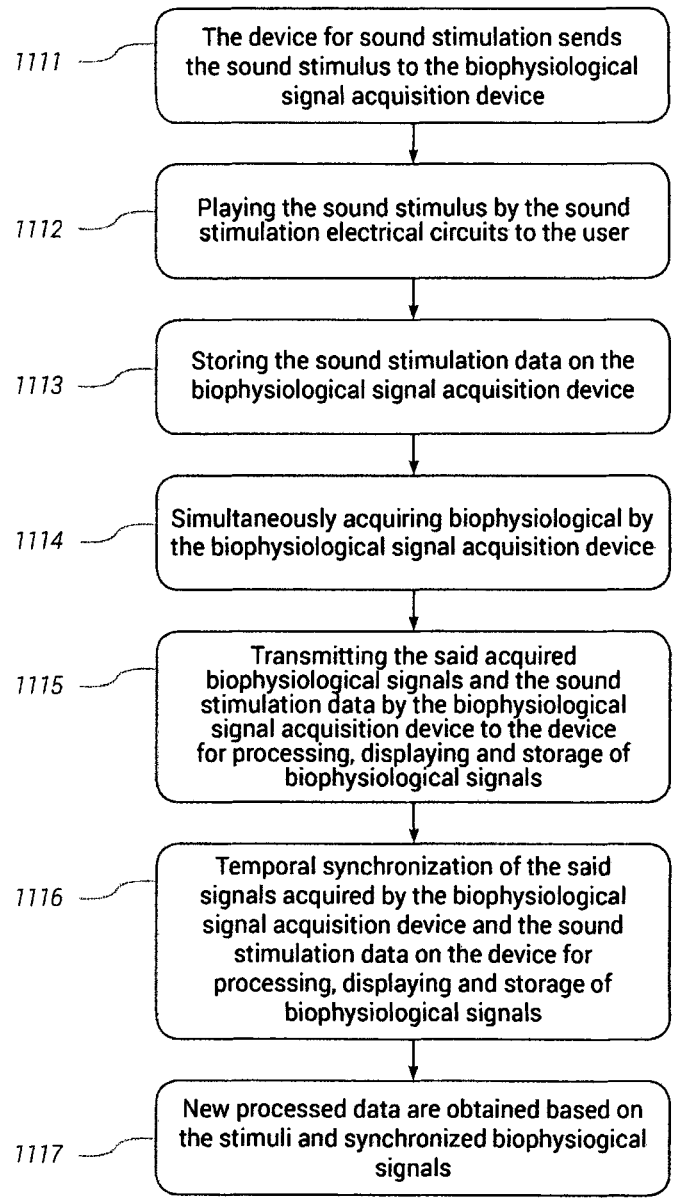
FIG. 11 is a flowchart of biophysiological signals acquisition as a result of biofeedback controlled with sound stimuli.

FIG. 11 is a complete operational diagram of the biophysiological signals acquisition process as a result of biological feedback induced by sound stimuli.

Step 1111: The device for sound stimulation sends a sound stimulus to the headphones that are embedded in the wireless head comprising the biophysiological signal acquisition device. The device for administering sound stimulation is essentially a smart phone. The device for sound stimulation may be, in particular, the same as the device for processing, display and storage of biophysiological signals. The Sound stimulation may be, in particular, played for the purpose of biological feedback via software applications for biological feedback. Sound stimulation may be, in particular, a simple sound stream content on the device for sound stimulation. For example, if the device for sound stimulation is a smart phone, sound stimulus could be music, streamed by any of the mobile applications for streaming music, or could be an output sound from the video or any other content that could be audible when played on a smart phone. Sound stimulation, therefore, may also have properties of cognitive, and not only the purely sound stimulation.

Step 1112: An audible signal is administered through the headphones that are embedded in the wireless head set comprising the biophysiological signal acquisition device.

Step 1113: The biophysiological signal acquisition device stores the sound stimulation data in the internal memory. The said data is, in particular, the exact time when the stimulus was released, the sound description and various other data.

Step 1114: The biophysiological signal acquisition device simultaneously acquires biophysiological signals from biophysiological sensors.

Step 1115: The biophysiological signal acquisition device transmits collected biophysiological signals, together with sound signals used for the sound stimulation, to the device for processing, display and storage of biophysiological signals.

Step 1116: The device for processing, display and storage of biophysiological signal processes the signals in a manner to be time-synchronized signals to sound stimulation and possibly performs additional processing of the received signals.

Step 1117: Based on the processing in Step 1116, the new biophysiological signals are obtained that may be displayed on the screen of the device for processing, display and storage of biophysiological signals, or they may be stored in the internal memory of the device for processing, display and storage of biophysiological signals or may be transmitted to the central server.

Processed biophysical signals are, in particular, mental states.

Figure 12:
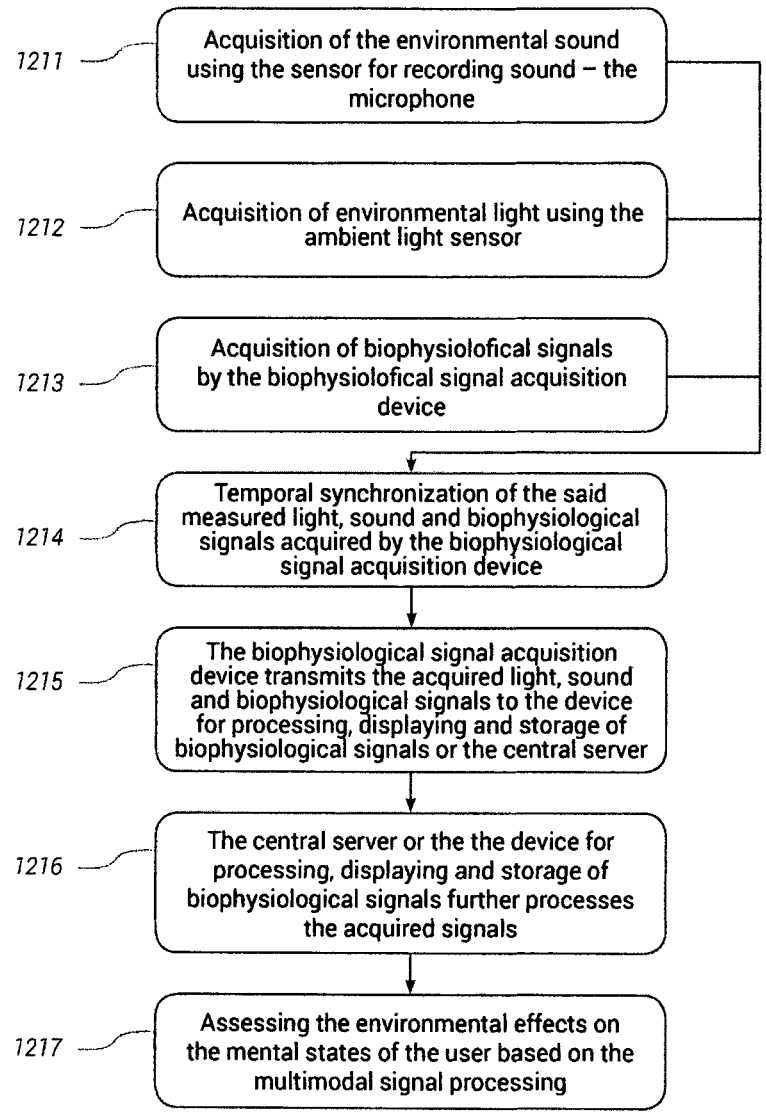
FIG. 12 is a flowchart of the biophysiological signals acquisition as a result of external environmental stimuli.

FIG. 12 is a complete operational diagram of acquiring biophysiological signals as a result of external stimuli from the environment.

Step 1211: The biophysiological signal acquisition device 21 accepts sound signals from the environment using sensors for the acceptance of sound from the environment 324.

Step 1212: the mobile device for acquisition of biophysiological signal 21 acquires ambient light using the sensors for acquiring ambient light 323.

Step 1213: The biophysiological signal acquisition device 21 acquires biophysiological signals from the sensor for acquisition of biophysiological signal 312, 313*a*, 313*b*, 316*a*, 316*b*, 317 and 318 as shown in the flowchart of FIG. 6.

Steps 1211, 1212 and 1213 may, essentially, be carried out simultaneously.

Steps 1211 and 1212 may, essentially, both be carried out or only one of them.

Step 1214: The biophysiological signal acquisition device 21 performs signal processing of the acquired signals in steps 1211, 1212 and 1213 in a way to time-synchronize signals from the sensors for collecting ambient light from the environment, the signals from the sensor for collecting sound from the environment and acquired biophysiological signals.

Step 1215: The biophysiological signal acquisition device performs further processing of the signals acquired in steps 1211, 1212 and 1213 and transmits them to the device for processing, display and storage of biophysiological signals or to the central server for further processing, display and storage of the said biophysiological signals.

Step 1216: the mobile device for processing, display and storage of biophysiological signals or the central server perform further processing of the signals obtained in steps 1211-1215.

Step 1217: The software application for multimodal signal processing processes the collected signals from the steps 1211 to 1216, and after their treatment the influence of environmental conditions on the mental state (cognitive processes and emotional condition) on users is determined.

The device for processing, display and storage of biophysiological signals is essentially a smart phone, or a computer, or other device that has, but not limited to, the possibility of wireless communication (e.g. Bluetooth), the screen display for recorded signals, a software application for processing of biophysiological signals and a memory for the storage of the biophysiological signals.

The Processing of biophysiological signals is essentially a set of algorithms of biophysiological signal processing in order to assess the mental states.

Figure 13:
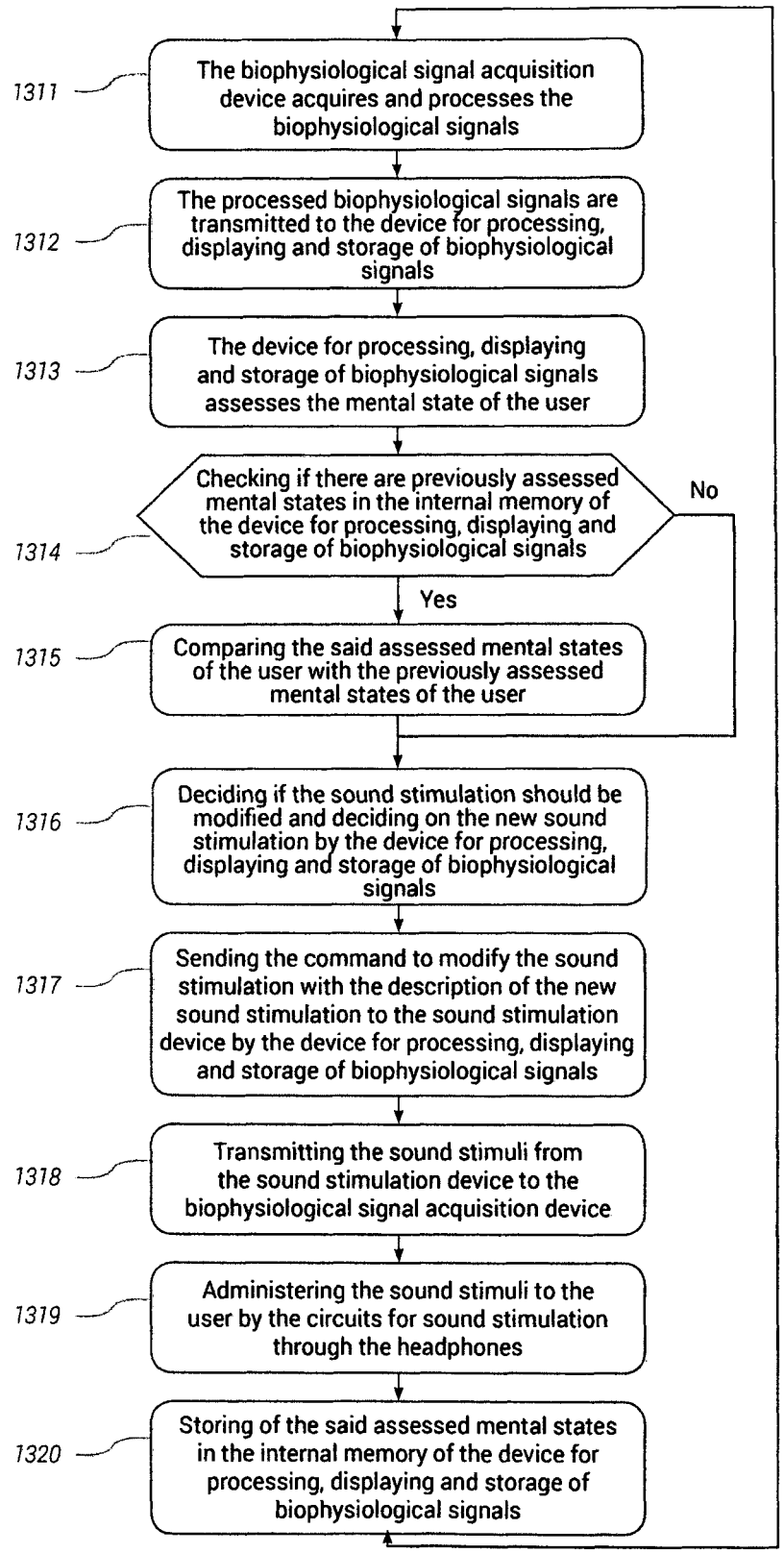
FIG. 13 is a flowchart of modifying a sound stimulus based on the measured mental states for the purpose of mental state modulation.

FIG. 13 is a complete operational diagram of modification of the sound stimulus on the basis of the measured mental state in order to change mental states, or to enhance or reduce the intensity of the current mental state.

Step 1311: The biophysiological signal acquisition device acquires biophysiological data from biophysiological sensors measuring electroencephalography, heart rate, blood oxygen saturation, electrodermal activity and body temperature and processes the said biophysiological signals.

Step 1312: The biophysiological signal acquisition device transmits the processed biophysiological signals to the device for processing, display and storage of biophysiological signals.

Step 1313: The device for processing, display and storage of biophysiological signals further processes biophysiological signals and thus determines the current mental state of the user.

Step 1314: It is checked whether there are already previous mental states stored in the memory of the device for processing, display and storage of biophysiological signals, in order to determine whether the received package of the acquired and processed biophysiological signals is the first such package, or the recording had started earlier.

Step 1315: In case there has been previously recorded and processed biophysiological signals and that the data on specific mental states has been stored in the memory of the device for processing, display and storage of biophysiological signal, the comparison is performed between the mental states from memory of the device for processing, display and storage of biophysiological signals recorded, with the newly determined mental states.

Step 1316: Based on the current determined mental states and the comparison with the previously predetermined mental states, the device for processing, display and storage of biophysiological signal determines whether it is necessary and how to modify the sound stimuli.

Step 1317: The device for processing, display and storage of biophysiological signal sends a command to the device for sound stimulation to change the sound stimulation, or retain the same stimulation, or to terminate the sound stimulation.

Step 1318: The device for sound stimulation transmits sound stimuli to the biophysiological signal acquisition device.

Step 1319: The biophysiological signal acquisition device administers the sound stimuli through the headphones that are embedded in the wireless headset comprising the biophysiological signal acquisition device.

Step 1320: The determined mental states are stored in the memory of the device for processing, display and storage of biophysiological signals for the purpose of comparison with the mental states determined in future iterations.

Steps 1311 to 1320 may be repeated an indefinite number of times. The device for processing, display and storage of biophysiological signals is essentially a smart phone. The device for administering sound stimulation is essentially a smart phone. The device for providing sound stimulation and the device for processing, display and storage of biophysiological signals are essentially the same device.

Figure 14:
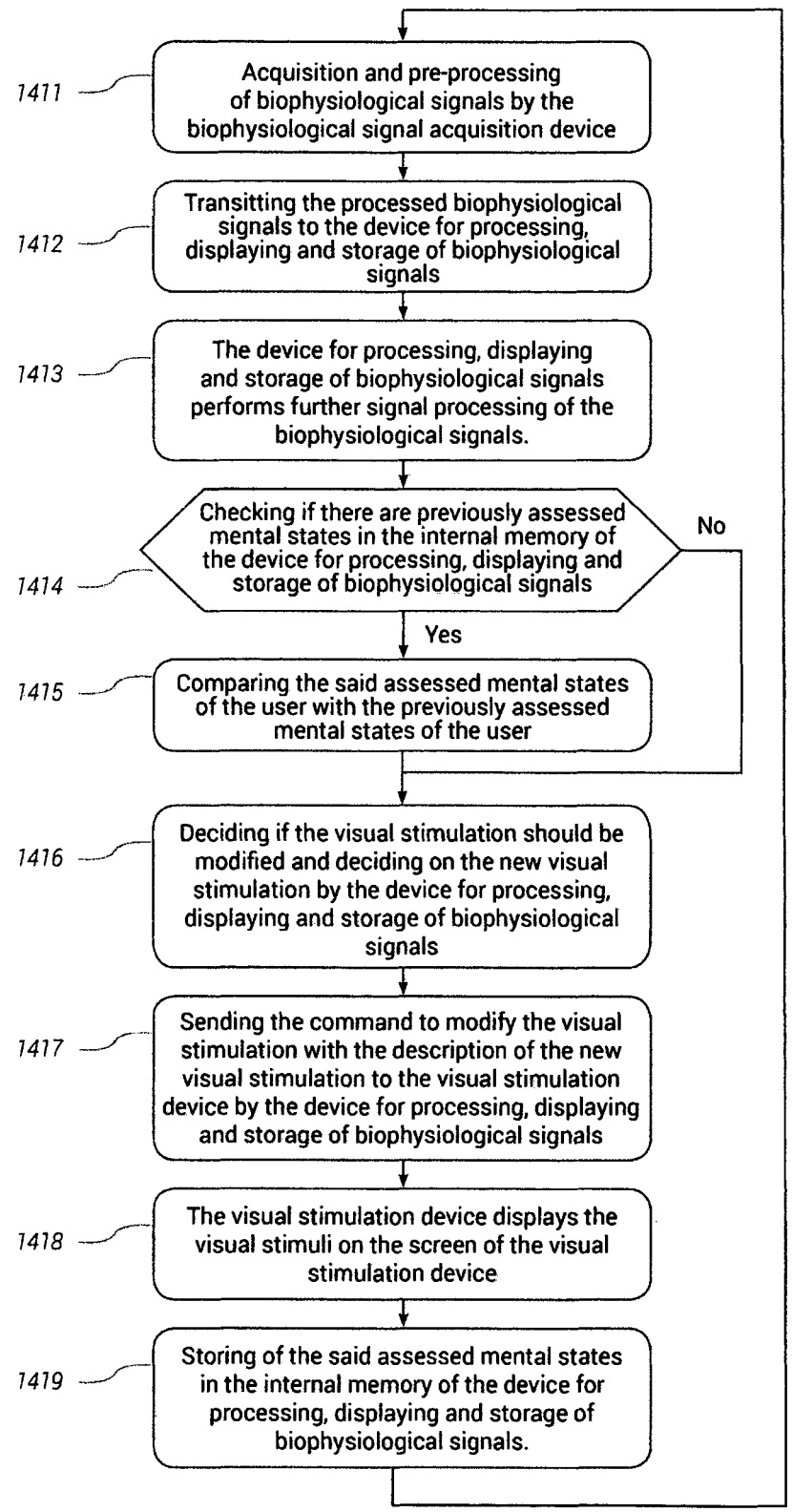
FIG. 14 is a flowchart of modifying a visual stimulus based on the measured mental states for the purpose of mental state modulation.

FIG. 14 is a complete operational diagram of modification of the visual stimulus on the basis of the measured mental state in order to change mental states, or to enhance or reduce the intensity of the current mental state.

Step 1411: The biophysiological signal acquisition device acquires biophysiological data from the biophysiological sensors for measuring electroencephalography, heart rate, blood oxygen saturation, electrodermal activity and body temperature and processes mentioned biophysiological signals.

Step 1412: The biophysiological signal acquisition device transmits the processed biophysiological signals to the device for processing, display and storage of biophysiological signals.

Step 1413: The device for processing, display and storage of biophysiological signals further processes biophysiological signals and thus determines the current mental state of the user.

Step 1414: It is checked whether there are already previous mental states stored in the memory of the device for processing, display and storage of biophysiological signals, in order to determine whether the received package of the acquired and processed biophysiological signals is the first such package, or the recording had started earlier.

Step 1415: In case there has been previously recorded and processed biophysiological signals and that the data on specific mental states has been stored in the memory of the device for processing, display and storage of biophysiological signal, the comparison is performed between the mental states from memory of the device for processing, display and storage of biophysiological signals recorded, with the newly determined mental states.

Step 1416: Based on the current determined mental states and the comparison with the previously predetermined mental states, the device for processing, display and storage of biophysiological signal determines whether it is necessary and how to modify the visual stimuli.

Step 1417: The device for processing, display and storage of biophysiological signal transmits a command to the device for visual stimulation, to change the visual stimulation or to maintain the same visual stimulation, or to stop visual stimulation.

Step 1418: The device for visual stimulation displays visual stimuli on the screen of the device for visual stimulation.

Step 1419: The storage of the determined mental states is performed in the memory of the device for processing, display and storage of biophysiological signals for the purpose of comparison with the mental states determined in future iterations.

Steps 1411 to 1419 can be repeated an indefinite number of times. The device for processing, display and storage of biophysiological signals is essentially a smart phone. The device for administering sound stimulation is essentially a smart phone. The device for providing sound stimulation and the device for processing, display and storage of biophysiological signals are essentially the same device.

A man mastering this field of technical equipment will realise that the embodiment of the invention, as shown in the drawings and described above only represents a non-limiting example.

The foregoing description of desired embodiments of the present invention is presented for purposes of illustration and description. Its purpose is not to exhaust or limit the invention to the precise forms or embodiments disclosed. Accordingly, the foregoing description should be regarded as illustrative rather than as restrictive.

Obviously, a lot of modifications will be apparent to those skilled in the field. Embodiments were chosen and described as the best way to explain the principles of the invention and the best ways for their implementation, so as to enable persons skilled in the field to understand the invention in various embodiments and various modifications, such as suits a particular use or intended use.

It is intended that the scope of the invention is to be defined by the patent claims appended to the end and by their equivalents, in which the terms used are in their broadest sense, unless otherwise is indicated. It should be understood that variations can be made in embodiments of the invention, as described by experts in the field without departing from the scope of the invention described herein, as defined in the following claims.

Moreover, no element and component in this description of the invention is not intended for the public, regardless of whether the element or component is explicitly listed in the following patent claims.

While the preferred embodiment of the invention has been set forth for the purpose of disclosure, modifications of the disclosed embodiment of the invention, as well as other embodiments thereof, may occur to those skilled in the art. Accordingly, the appended claims are intended to cover all embodiments, which do not depart from the spirit and scope of the invention.

The invention claimed is:

1. A wearable biophysiological signal acquisition device comprising:
a plurality of EEG electrodes configured to measure EEG activity,
at least one reference electrode,
at least one ground electrode,
an axle adapted to extend around a head of a wearer,
first and second curved portions connected to the axle, and at least one headphone configured to supply sound stimulation to the wearer, wherein a first group of the plurality of EEG electrodes is mounted on the first curved portion, and a second group of the plurality of EEG electrodes is mounted on the second curved portion, the axle being configured to press the first group of EEG electrodes against skin behind a first ear of the wearer and to press the second group of EEG electrodes against skin behind a second ear of the wearer, to permit EEG activity of the wearer to be measured by the plurality of electrodes through the skin behind the ears of the wearer, wherein the measured EEG activity is used to assess a mental state of the wearer.

2. The wearable biophysiological signal acquisition device recited in claim 1, wherein the axle is configured to hold the plurality of electrodes firmly to the head of the wearer.

3. The wearable biophysiological acquisition device recited in claim 1, further comprising at least one further sensor selected from the group: at least one electrode for measuring electrodermal activity, at least one ground electrode for measuring electrodermal activity, at least one light sensor for transmissive measurement of pulse oximetry, at least one light sensor for reflective measurement of pulse oximetry, at least one body temperature measurement sensor, at least one ambient light sensor, at least one sensor for recording sound, at least one movement sensor, at least one accelerometer, at least one gyroscope at least one magnetometer, and a GPS device.

4. The wearable biophysiological acquisition device recited in claim 1, wherein the biophysiological signal acquisition device is integrated in a wireless headset that comprises the at least one headphones.

5. The wearable biophysiological acquisition device recited in claim 1, wherein a body of the biophysiological signal acquisition device comprises input electric circuits for signal acquisition of one or more of: biophysiological signal acquisition and environmental signal acquisition.

6. The wearable biophysiological acquisition device recited in claim 5, wherein the input electric circuits for biophysiological signal acquisition comprise: electroencephalographic signal acquisition circuits.

7. The wearable biophysiological acquisition device recited in claim 1, wherein the device further comprises one or more speakers for sound stimulation.

8. The wearable biophysiological acquisition device recited in claim 1, further comprising a processor operable to estimate one or more mental states of the user based on the acquired biophysiological signals.

9. A system comprising:
a wearable biophysiological acquisition device comprising:
a plurality of EEG electrodes configured to measure EEG activity,
at least one reference electrode,
at least one ground electrode,
an axle adapted to extend around a head of a wearer, first and second curved portions connected to the axle, and
at least one headphone configured to supply sound stimulation to the wearer,
wherein a first group of the plurality of EEG electrodes is mounted on the first curved portion, and a second group of the plurality of EEG electrodes is mounted on the second curved portion, the axle being configured to press the first group of EEG electrodes against skin behind a first ear of the wearer and to press the second group of EEG electrodes against skin behind a second ear of the wearer, to permit EEG activity of the wearer to be measured by the plurality of electrodes through the skin behind the ears of the wearer, and
a mobile device for receiving EEG signals from the wearable biophysiological acquisition device,
wherein system is operable to use the measured EEG activity to assess one or more mental states of the wearer.

10. The system recited in claim 9, wherein the mobile device for receiving biophysiological signals comprises a processor that is operable to execute one or more biophyisiological signal processing algorithms for the purpose of extracting the one or more mental states.

11. The system recited in claim 9, wherein the mobile device for receiving biophysiological signals comprises a personal computing device (e.g. a smartphone device).

12. The system recited in claim 9, further comprising a central server, wherein the central server comprises a processor operable to execute one or more biophyisiological signal processing algorithms for the purpose of extracting the one or more mental states.

13. The system recited in claim 9, wherein the system is operable to supply a stimulus to the wearer of the wearable biophysiological acquisition device, and wherein the wearable biophysiological acquisition device is operable to measure electrophysiological activity of the wearer in response to the stimulus, such that the system is operable to use the measured electrophysiological activity to assess a mental state of the wearer in response to the stimulus.

14. The system recited in claim 13, wherein the stimulus is selected from: a visual stimulus, an audible stimulus, both a visual and an audible stimulus.

15. The mobile system recited in claim 13, further comprising a central server, wherein the central server is operable to store biophysiological signals received from the wearable biophysiological acquisition device in a central database, and wherein, in response to a user identification to the central server by the mobile device the central server downloads stored signals from the central database and transmits the said signals to the mobile device.

16. The system recited in claim 15, wherein the system is operable to:
acquire biophysiological signals using the wearable biophysiological signal acquisition device,
process the said biophysiological signals and assess a first mental state of the wearer,
compare the said assessed first mental states with the previously assessed mental states of the wearer that are stored in the system
determine whether to modify the said first mental state,
provide a stimulus to the wearer to modify the first mental state of the wearer,
acquire further biophysiological signals using the wearable biophysiological signal acquisition device,
process the said biophysiological signals and assess a second mental state of the wearer.

17. The system of claim 13, wherein the system is operable to:
provide a first stimulus to a wearer of the biophysiological signal acquisition device,
acquire first biophysiological signals simultaneously with the provision of the first stimulus,
use the first biophysiological signals to assess a first mental state of the user in response to the first stimulus, provide a second stimulus to the wearer of the biophysiological signal acquisition device, acquire second biophysiological signals simultaneously with the provision of the second stimulus, use the second biophysiological signals to assess a second mental state of the user in response to the second stimulus.

18. The system of claim 17, wherein the second stimulus is selected to alter the mental state of the user.

19. The system of claim 17, wherein the first and second stimuli are visual stimuli, and are provided to the wearer on a screen of the mobile device.

20. The system of claim 17, wherein the first and second stimuli are audible stimuli, and are provided to the wearer through headphones of the wearable biophysical signal acquisition device.

21. The system of claim 13, wherein the stimulus is selected from the group: a visual stimulus shorter than 1 second, a sound stimulus shorter than 1 second, a visual stimulus longer than 1 second, a sound stimulus longer than 1 second, a video, music, visual stimuli that cause epileptic seizures, stimuli for visual therapy, stimuli for music therapy, and a combination of these stimuli.

22. The system of claim 13, wherein the system is operable to acquire stimulation data when a stimulus is provided to the wearer.

23. The system of claim 22, wherein the stimulation data is one or more of the time of the stimulus, the stimulation type, a description of the stimulation.

24. The system of claim 9, further comprising a microphone for recording environmental sound in the vicinity of the wearer and an ambient light sensor for recording environmental light in the vicinity of the wearer, wherein the system is operable to:

acquire environmental sound data using the microphone, acquire environmental light data using the ambient light sensor, acquire biophysiological signals using the biophysiological signal acquisition device, determine a mental state of the wearer in response to the said environmental light and environmental sound.

25. The system recited in claim 24, wherein the acquisition of the ambient light, environmental sound and biophysiological signals is performed simultaneously.

26. The system recited in claim 9, wherein the biophysiological signals are processed using one or more processing algorithms operable to extract one or more of: the band power of one or more EEG frequency bands (alpha, beta, gamma, delta and theta) of the wearer, event related potentials from EEG signals of the wearer, a heart rate of the wearer, a blood oxygenation level of the wearer, an electrodermal activity of the wearer, a body temperature of the wearer, epileptiform activity.

27. The system recited in claim 26, wherein the said mental state of the wearer is estimated using mathematical formulae that take into account the power of EEG frequency bands, heart rate, blood oxygenation, electrodermal activity and body temperature of the user.

28. The system recited in claim 9, wherein the mental state is one or more of a stress level of the wearer, a change in a stress level of the wearer, a happiness level of the wearer, a change in a happiness level of the wearer, a focus level of the wearer, a change in the focus level of the wearer, a tiredness level of the wearer, a change in the tiredness level of the wearer, a relaxation level of the wearer, a change in the relaxation level of the wearer, a productivity level of the wearer, a mental workload of the wearer, and a mental engagement.

29. A wearable biophysiological signal acquisition device comprising:

a plurality of EEG electrodes configured to measure EEG activity, at least two reference electrodes, at least one ground electrode, input circuits for biophysiological acquisition connected to the EEG electrodes, reference electrodes and ground electrode, an axle adapted to extend around a head of a wearer, first and second curved portions connected to the axle, and at least one headphone configured to supply sound stimulation to the wearer, wherein a first group of the plurality of EEG electrodes is mounted on the first curved portion, and a second group of the plurality of EEG electrodes is mounted on the second curved portion, the axle being configured to press the first group of EEG electrodes against skin behind a first ear of the wearer and to press the second group of EEG electrodes against skin behind a second ear of the wearer, to permit EEG activity of the wearer to be measured by the plurality of electrodes through the skin behind the ears of the wearer, wherein the two reference electrodes are each located adjacent a different ear of the wearer, and are at least one of:

(i) physically separated inside the input electric circuits for biophysiological signal acquisition, and (ii) short circuited inside the input electric circuits for biophysiological signal acquisition, and wherein the measured EEG activity is used to assess a mental state of the wearer.

* * * * *